United States Patent [19]

Marx

[11] Patent Number: 5,898,037
[45] Date of Patent: Apr. 27, 1999

[54] FORMULATIONS OF MAGNESIUM COMPOUNDS FOR LOCAL APPLICATION AND METHODS OF TREATMENT USING THE SAME

[76] Inventor: Alvin J. Marx, 511 Mirepoix, San Antonio, Tex. 78232-1951

[21] Appl. No.: 08/678,151

[22] Filed: Jul. 11, 1996

Related U.S. Application Data

[63] Continuation of application No. 08/311,599, Sep. 23, 1994, abandoned, which is a continuation-in-part of application No. 07/975,786, Nov. 13, 1992, abandoned.

[51] Int. Cl.$^6$ .............................. A61K 7/16; A61K 7/22; A61K 33/04
[52] U.S. Cl. .............................. 424/49; 424/54; 424/709
[58] Field of Search .............................. 424/49, 54, 709

[56] References Cited

U.S. PATENT DOCUMENTS

| | | | |
|---|---|---|---|
| 3,988,433 | 10/1976 | Benedict | 424/53 |
| 4,024,237 | 5/1977 | Eichel et al. | 424/49 |
| 4,183,914 | 1/1980 | Gaffar et al. | 424/49 |
| 4,241,049 | 12/1980 | Colodney et al. | 424/54 |
| 4,244,698 | 1/1981 | King et al. | 23/313 |
| 4,517,701 | 5/1985 | Stanford | 15/106 |
| 4,701,320 | 10/1987 | Hasegawa et al. | 424/54 |
| 4,776,500 | 10/1988 | Ford | 222/402.1 |
| 4,812,306 | 3/1989 | Cocherell et al. | 424/52 |
| 4,971,782 | 11/1990 | Rudy et al. | 424/53 |
| 5,004,596 | 4/1991 | Cocherell et al. | 424/52 |

*Primary Examiner*—Theodore J. Criares
*Attorney, Agent, or Firm*—Nixon, Hargrave, Devans & Doyle LLP; Grant E. Pollack

[57] ABSTRACT

This invention provides novel pharmaceutical compositions which comprise magnesium compounds in hypertonic amounts. These compositions are formulated for local application for the treatment of conditions such as acne, arthritis, periodontal disease ophthalmic conditions (e.g., conjunctivitis), hemorrhoids, vaginal infections and inflammation, and ulcerative colitis. The compositions are formulated with an acceptable dermatological, oral, rectal, vaginal, or ophthalmic carrier for use in treating these conditions. Also provided is a method for treating asthma wherein the magnesium compositions are administered by inhalation. Any of these treatments, and especially that for asthma, can be supplemented with oral administration of magnesium.

12 Claims, No Drawings

5,898,037

FORMULATIONS OF MAGNESIUM COMPOUNDS FOR LOCAL APPLICATION AND METHODS OF TREATMENT USING THE SAME

This application is a continuation of application Ser. No. 08/311,599, filed Sep. 23, 1994, now abandoned, which is a continuation-in-part of application Ser. No. 07/975,786, filed Nov. 13, 1992, now abandoned, the disclosure of which is incorporated herein by reference.

BACKGROUND OF THE INVENTION

1. Field of the Invention

The present invention relates to novel pharmaceutical compositions including magnesium compounds and to novel methods of treatment using the same, and is particularly directed to compositions for local application, such as topical, inhalational, rectal administration, including optionally systemic administration as a supplement thereto, and to novel treatments using the same.

2. The State of the Art

The magnesium cation is an essential mineral for many animals, including mammals, and especially for humans. As used herein, the term "magnesium" is intended to mean the salt or free ion form (as opposed to the non-ionic form). As such, magnesium is also a cofactor in numerous enzymatic reactions. It is involved in phosphate transfer from ADP and ATP muscle contractility, and neuronal transmission. The majority of magnesium in the human body is located in the bones in the form of phosphates and carbonates, and the remainder is found principally in the liver and muscles; red blood cells also contain magnesium. Magnesium inhibits nerve impulses and relaxes muscle contractions, thereby functioning antagonistically to calcium. On the other hand, like calcium, magnesium can bind phosphates and can substitute for calcium as a bone or tooth mineral. Accordingly, systemic (oral) calcium supplementation is often administered when magnesium is given systemically.

Various magnesium compounds have been used via intramuscular, oral, and intravenous routes of administration For example, magnesium acetate is used as a source of magnesium and as an acetate supply of bicarbonate in hemodialysis or peritoneal dialysis solutions; magnesium chloride is likewise used in dialysis solutions.

Magnesium gluconate has been used in the treatment of myocardial infarction. Magnesium gluconate has also been indicated for use as an adjunct in alleviating eclampsia, in the treatment of fetal distress, and in controlling premature/preterm labor where adrenergic receptor antagonists (e.g., ritodrine) are contra-indicated or poorly tolerated.

Magnesium sulfates commonly available in dry form as epsom salts, has been indicated in the form of a paste for use in the treatment of inflammatory skin conditions. However, prolonged or repeated use has been found to damage the skin. It has been postulated that magnesium sulfate paste may prevent bacterial growth by creating a strong osmotic gradients whereby the bacteria are killed effectively by dehydration; recent reports have suggested the same osmotic antibacterial effect when using salt or sugar (as reported for thoracic surgical wounds). Magnesium sulfate also has been indicated for internal use in treating bronchial asthma and cardiovascular disorders (eg., cardiac arrhythmia hypertension, and tachycardia)

Magnesium also has been taken internally and has been postulated to prevent dental caries, although experimental studies are equivocal. (H. Luoma, "The role of magnesium in the aetiology and prevention of caries: some new findings and implications," *Magnesium Research*, 1, 3/4, 223–230 (1988).)

Direct injection and oral administration of magnesium sulfate has been suggested for treating soft tissue calcification. (L. Steidl et al., "Soft tissue calcification treated with local and oral magnesium therapy," *Magnes Res.* (England), June 1990, 3(2), p. 113–9.)

Inhaled magnesium sulfate has been found to reduce the histamine bronchoprovocation test in asthmatics, and has been noted to be useful in decreasing bronchial hyper-reactivity (that is, in attenuating histamine-induced broncho-constriction). (G. Rolla et al., "Dose-Related Effect of Inhaled Magnesium Sulfate on Histamine Bronchial Challenge in Asthmatics," *Drugs Exptl. Clin. Res.*, XIV(9) 609–612 (1988), and "Reduction of histamine-induced bronchoconstriction by magnesium in asthmatic subjects," *Allergy*, 42, 186–188 (1987).) The authors recommend that the aerosol solution be iso-osmolar and at near-physiological pH. Inhaled magnesium sulfate also has been investigated as an adjuvant in treating asthma. (H. Manzke et al., "Magnesium sulfate as adjuvant in beta-2-sympathomimetic inhalation therapy of bronchial asthma," *Pneumologie* (Ger.), October 1990, 44(10), p. 1190–2.)

The topical use of magnesium salts has been suggested for the treatment of burns caused by hydrofluoric acid.

The topical use of magnesium chloride has been suggested as an alternative to commonly used corticosteroids for treating common skin diseases. (P. W. M. Copeman, "New non-steroid non-antibiotic skin medicaments," *Brit. Med. J.*, Nov. 1, 1979, p. 264.) The authors disclose a cream or lotion including magnesium chloride in an amount of about 1.5%, and appear to be particularly concerned with inhibiting infection by gram-negative bacteria. Likewise, and as noted above, the use of magnesium sulfate paste and sugar have been suggested for inhibiting bacterial growth by creating a strong osmotic gradient. (P. Lowthian et al., "Sterculia for Wound Healing" (letter), *The Lancet*, Sep. 23, 1985, p.1186.)

Using a combination of magnesium and aluminum hydroxide has been suggested to inhibit localized dermal reactions to transdermal clonidine. The investigators found this combination less effective than hydrocortisone in alleviating the local dermatitis. (M. K. Ito et al., "Skin pretreatment and the use of transdermal clonidine," *Am. J. Med*, Jul. 18, 1981, 91(1A), p. 42S–49S.)

In general, when magnesium salts have been considered useful for pharmacotherapy, such salts have been used in solution having a maximum concentration that is isotonic. It is conventional pharmacological protocol to make solutions that are concentrated, at most, at the isotonic level, and more conventionally such solutions have a concentration that is hypotonic; hypertonic solutions are avoided because of their dehydrating and irritating effects.

SUMMARY OF THE INVENTION

It has been discovered that local application of magnesium is useful for treating a number of conditions in mammals, including humans. Some of these conditions were not previously treated with magnesium even by other routes of administration.

It is an object of the present invention to provide compositions suitable for the local application of magnesium compounds and useful for the treatment and/or prophylaxis of various conditions.

It is a further object of this invention to provide improved compositions for local application, which improvement includes the addition of at least one highly soluble magnesium compound to the composition.

Yet another object of this invention is to provide novel curative, ameliorative, and/or prophylactic treatments especially for the conditions of acne, asthma, periodontal disease, and arthritis, and also for conjunctivitis, ulcerative colitis, and vaginitis, by the local administration of magnesium.

A further object of this invention is to provide such novel treatments by a combination of both local and systemic administration of magnesium compounds.

Still another object of this invention is to provide a safe, economical, and non-toxic medication that is useful for the local treatment of various host conditions, and moreover is as simple to use as conventional over-the-counter medications.

Briefly, the novel compositions of the present invention comprise an at least hypertonic, if not saturated, solution of at least one highly soluble magnesium compound, and optionally include one or more active and/or inactive ingredients typically included in compositions intended for the treatment of a particular condition.

The novel method of the present invention generally comprises the application of the novel composition just mentioned to the local portion of the host to be treated, and then allowing the composition to dry. This treatment method optionally includes local administration of magnesium supplemented with oral administration. Any of these treatments can be supplemented with oral administration of magnesium.

DETAILED DESCRIPTION OF PREFERRED EMBODIMENTS

The present invention generally provides pharmaceutical compositions that include a saturated solution of at least one magnesium compound. As used herein, "magnesium" or generally a compound thereof includes elemental magnesium ion in the form of any pharmaceutically acceptable salt, chelate, or solvate thereof. A preferred magnesium compound is the sulfate salt, known commonly as epsom salts. Other suitable magnesium salts include chlorides, oxides, hydroxides, ascorbates, aspartates, gluconates, lactates, and the like. These salts are generally available in pharmaceutical grades as noted in standard pharmacopoeias.

A saturated, or at least hypertonic, solution comprised of one or more of the magnesium compounds is preferred. Because of the occasional local irritation of a sensitive area by the saturated solution, the compositions of this invention may include amounts of the magnesium compound(s) lower than required for saturation. It is generally preferred to provide as high a concentration of the magnesium as possible without causing local irritation or toxicity. The skilled artisan can easily determine the maximum amount of a particular magnesium compound that can be dissolved in solution. For magnesium sulfate, a preferred magnesium compound, generally about 50% by weight will provide a saturated aqueous solution. Magnesium sulfate is generally soluble at 26 g per 100 cc of water at 0° C., and at about 72 g per 100 cc of water at 1000 C. Common industry guides, such as *The Merck Index* (Merck Co., Rahway, N.J.) provide tables of various salts and their isotonic solution data. By the term "highly soluble" is meant a salt that is soluble in the solution or vehicle in an amount of at least about 50 grams per liter (sees eg., R. K. McAlpine et al., *Qualitative Chemical Analysis* (New York: D. Van Nostrand Co., Inc., 1933) p. 131, where their definition of "soluble" is used herein as "highly soluble"). Thus, the highly soluble magnesium salts contemplated include those which are soluble in the vehicle, not those which can be "solubilized" because such salts are dispersed in a non-ionized form and are not truly solvated by the medium (it is the solubilizing material that is actually solubilized).

The solution or vehicle into which the magnesium compound is dissolved should be an acceptable pharmaceutical or dermatological carrier for application to the local area. The vehicle is preferably aqueous-based, and cream, gel, lotion, or wet pad formulations are most preferred. Vehicles which are suitably combined with water or which can be used individually or in combination as the vehicle include, for example, gel-water soluble "greaseless ointments" such as polyethylene glycol, cream bases including microcrystalline dispersions of long chain fatty acids in alcohol, ointments (such as white petrolatum based), and water. Thus, any one or any combination of magnesium compounds that are water soluble or can be dispersed in a suitable vehicle, that are pharmaceutically acceptable, and that are chemically compatible with the other ingredients of the composition can be used.

These compositions are formulated for local administration. As used herein "local" administration includes direct topical application, such as to the eye (drops) and the oral cavity (mouthwash), local topical application, such as for joint pain wherein the composition is applied to the skin in the area of joint pain, and similar topical application where local effects are desired. (eg., rectal suppositories, medicated tampons for vaginal application). Local administration also includes inhalational administration to affect the airway and lungs directly. Accordingly, the present invention contemplates action of the magnesium in the formulation directly on the tissues to which it is applied, and to nearby (local) tissues via diffusion, as required to treat the affected area.

The magnesium compound(s) also can be provided in the form of a cream, gel, lotion or wet pad. Typically, creams, gel, and lotions provide longer contact with the skin due to their viscosity, and thus provide better absorption. Also, creams and lotions can be formulated with various wetting agents or penetration enhancers to further increase the penetration of the magnesium to the affected area. Although reference is made herein to solutions of magnesium compounds that are "saturated," the maximum amount of magnesium in emulsions, suspensions, and the like should be not more than about 50% by weight. Accordingly, when the present compositions are formulated as creams, lotions, gels, and the like, the amount of magnesium should be determined on the basis of the liquid (eg., aqueous or aqueous-based) phase present, and the time the compound will generally be expected to remain on the skin.

As described in more detail below, the compositions of the present invention, when formulated for the treatment of a specific host condition, preferably include one or more active and/or inactive ingredients typically found in such compositions. For example, a composition for treating acne can include benzoyl peroxide or another antibacterial as an active ingredient, and/or a corticosteroid as an anti-inflammatory, as well as an emollient and/or humectant, in the magnesium-containing formulation.

Magnesium is known to stabilize membranes and prevent degranulation of mast cells. It is postulated that magnesium also interferes with the degranulation of white cells, thereby inhibiting the inflammation and/or degeneration of tissue.

Interrupting this vicious cycle of inflammation, white cell degranulation, and further inflammation is believed to allow healing and regeneration to take places.

The various compositions in which the invention can be embodied may have a number of adjuvants in addition to (or in place of) those already mentioned. Adenosine (commercially available as Adenocard), or phosphate derivatives thereof, such as ADP and ATP, are preferred adjuvants; magnesium is a cofactor in the ADP→←APT conversion process. Another adjuvant is thyroxine (preferably the L-Form), which can be added in amounts which are less than those that would result in hyperthyrodism). Both adenosine (and its derivatives) and thyroxine are independently useful adjuvants in combination with all of the utilities mentioned for the present composition, in both topical and systemic administration.

Topical formulations according to the present invention may also contain a cosmetically acceptable surfactant, such as a lauryl sulfate salt (eg., sodium lauryl sulfate), simethicone (dimethyl polysiloxane) and the like, preferably in amounts of from 0.05% to 5% by weight of the composition.

Of course, compatible additives such as preservatives, stabilizers, fragrances, color, emollients demulcents, thickeners, opacifiers, and/or humectants may also be added as desired.

The present saturated compositions are preferably applied in a liquid solution and allowed to dry, rather than administered as a soak. Traditionally, epsom salts have been applied topically in low concentration as a wet soak, because a soak using a saturated epsom salt solution for longer than about fifteen minutes will likely cause local dermatitis.

In other embodiments, it is preferred to administer the instant compositions with the aid of vibration, preferably in the range of 50 to 1000 Hz (300–60,000 cycles per minute); for oral applications, the vibration frequency is preferably 50–100 Hz, more preferably 80–85 Hz, and for other topical applications the vibration frequency is preferably 300–700 Hz, more preferably 400–600 Hz. Vibrational application can be performed using conventional electric toothbrushes (for oral application), muscle massagers (eg., MusclePro from Sunbeam-Oster Co., Inc., Hattiesburg, Miss.) and similar devices commercially available for consumer use.

The present invention will now be described in more detail with reference to the following examples, which are meant to illustrate the invention and not intended to be limiting with respect to the particular compounds, their amounts or the particular procedures described.

Treatment of Acne.

The general etiology of acne includes a bacterial infection of the facial pores and hair follicles.

A suitable composition according to this invention which is useful for treating acne, and other inflammatory and/or allergic skin conditions, preferably includes 0.1–50% of magnesium sulfate as the active agent, although higher concentrations may also be suitable. (Unless otherwise noted, all percentages used herein are based on weight.) Administration is preferably twice daily. The composition preferably includes other conventional active ingredients such as zinc sulfide or sodium thiosulfate to assist in resolving comedones (blackheads) and benzoyl peroxide as an antibacterial. Corticosteroids and isotrentinoin may also be added depending upon the severity of the condition for a particular host. Preferred optional active ingredients include hydrocortisone in effective amounts up to about 5%, more preferably in amounts of about 1%. These formulations may also include an antibiotic such as erythromycin (in amounts up to about 2%, with 0.5% being more preferred) or clindamycin (in amounts up to about 5% with 1% being more preferred).

This composition may also include such conventional additives as CMC (carboxymethylcellulose), methyl cellulose, and the like at 0.01% to 5% as part of the carrier to maintain the treatment solution, after application, in the locale being treated. Other possible additives include glycerin and/or zinc oxide as a soothing agent. Still other optional ingredients include surfactants (eg., Polysorbate 80, cetyl pyridinium chloride, Poloxamer 407, sodium lauryl sulfate, and the like) or such compounds as DMSO (dimethyl sulfoxide) to enhance the penetration of the magnesium compound and other optional active ingredients through the dermal tissues, as well as keratolytic agents (eg., salicylic acid). The vehicle may also include one or more of a number of silicone fluids used conventionally in dermatologic and cosmetic formulations, and which appear to be practically inert and non-toxic. Other suitable vehicles include ethanol, propylene glycol, glycerine, water (preferably deionized if not distilled), and compatible mixtures thereof. The mixture can be thickened with conventional agents, such as various gums (e.g., xanthan gum) made into a soap using a conventional foaming agent (e.g., sodium lauryl sulfate), and so on.

The solution of the magnesium compound is formulated into a desired form as a solution, cream, lotion, ointment, foam, soap, stick, suspension, or emulsion that is pharmaceutically acceptable and aesthetically pleasing. General methods for providing such formulations, and others, can be found in such references as *Remington's Pharmaceuticals*. In another embodiment, a towelette, swab, or other solid absorbent article may be moistened or saturated with the novel solution of the magnesium compound and sealed into a unit dose package for easy transportation and use when required.

This composition is applied to the facial areas to be treated and is allowed to dry. Generally, the composition should be applied 1–5 times each day for a composition including 0.1–50% magnesium (magnesium compound).

| Acne Wipe | | Wt. % |
|---|---|---|
| Salicylic acid[1] | keratolytic agent | 1.0 |
| Ethanol SD40 95%[2] | vehicle | 15.0 |
| Propylene Glycol[3] | vehicle | 6.0 |
| Glycerine 96%[4] | vehicle | 7.5 |
| Magnesium Sulfate Heptahydrate USP | active ingredient | 12.5 |
| Water (D.I.) | vehicle | 58.0 |

[1]USP grade, from Rhone Poulenc, Monmouth Junction, NJ.
[2]Grain Processing Corp., Muscatine, ID
[3]Arco Chemical, Philadelphia, PA.
[4]USP grade, from Henkel Emery Group, Cincinnati, OH.

This composition is intended to be applied by using pads or other cosmetic wipes soaked in the composition.

| Acne Gel | | Wt. % |
|---|---|---|
| Salicylic acid (USP) | keratolytic agent | 1.0 |
| Ethanol SD40 95% | vehicle | 15.0 |
| Propylene Glycol (USP) | vehicle | 6.0 |
| Glycerine 96% (USP) | vehicle | 7.5 |
| Xanthan Gum[5] | thickener | 0.9 |

-continued

Acne Gel

| | | Wt. % |
|---|---|---|
| Magnesium Sulfate Heptahydrate USP | active ingredient | 12.5 |
| Water (D.I.) | vehicle | 57.1 |

[5]Kelco Div. of Merck, San Diego, CA.

Anti-Wrinkle Skin Treatment

Another utility of these novel magnesium formulations is for treating wrinkled skin, that is, ameliorating the effects of aging and similar conditions (e.g., excess sun exposure) on the skin. These formulations will contain up to 50% of magnesium sulfate as the preferred compound, preferably at least 5% by weight, and more preferably 10–30% of the magnesium compound. Administration is preferably twice daily. Additional active ingredients include 4–12% of an exfoliant such as α-hydroxy ethanoic acid or glycolic acid, a compound such as glycerin or polyethylene glycol for restoring the skin resilience, a soothing agent such as urea (in amounts up to about 15%, preferably about 10%), other skin conditioners such as mineral oil and lanolin, and compatible mixtures thereof; still further optional ingredients include preservatives and/or emulsifiers/surfactants such as parabens and sodium lauryl sulfate.

These anti-wrinkle formulations are preferably provided in the form of a cream, lotion, gel, or moistened towelette. One preferred formulation is as an ointment or cream including as the base a vitamin A and D ointment (a standard product), which provides further wrinkle-reducing benefits due to the vitamins. It is also preferred to add up to 20,000 I.U. of vitamin E as a skin conditioner and anti-oxidant. Another preferred formulation is an emulsion including an aqueous phase comprising at least the magnesium compound and a non-aqueous phase comprising vitamins A, D, and/or E, and/or derivatives thereof; a typical derivative for vitamin A is a retinoic acid such as is available as RETIN-A brand cream. Such an emulsion would form the base for the anti-wrinkle formulation. Fragrance, colorants, and/or texturizers compatible with the formulation can be used as desired.

After-Shave Lotion or Shaving Cream or gel.

The foregoing composition for treating acne can be modified to formulate a medicated shave lotion or shaving cream. Reformulation for an after-shave lotion generally includes the addition of a not insignificant amount of alcohol to the base carrier as well as the addition of color and fragrance. The amount of magnesium, as in the acne preparations, should be in the range of 0.1% to 50%. Likewise, the after-shave lotion can be provided in unit packages of moistened towelettes.

When reformulated for use as a shaving cream, such a composition would also include surfactants and foaming agents typically found in shaving preparations, or the magnesium compound may be provided in a gel or liquid shaving base.

Either of these shaving formulations may include emollients and/or demulcents.

Treatment of Arthritis—External Analgesic.

The two most common types of arthritis are osteoarthritis and rheumatoid arthritis. In both conditions there is inflammation of the joint cavity (synovium), which also appears to involve the degenerative cycle mentioned above regarding degranulation, inflammation, and subsequently further degranulation. The novel compositions are also useful for treating conditions such as extra-articular rheumatism, neuralgia, neuritis, sore muscles, joint pain, sprains, muscle cramps, and other painful musculo-skeletal conditions.

A novel composition for treating such conditions is preferably a 50% magnesium sulfate solution (saturated) as previously described. An alternative embodiment is the administration of a 25% magnesium sulfate composition (e.g., dispersed in carboxymethylcellulose, "CMC") administered twice daily in combination with a 50% magnesium sulfate solution administered once daily. Other active ingredients may include one or more conventional analgesics and/or anti-inflammatories, such as hydrocortisone or another corticosteroid in amounts generally of 0.5–5%, methyl salicylate (or similar aspirin derivatives) and/or ibuprofen in amounts up to about 15%. When formulating composition including compounds which do not easily dissolve in water (e.g., ibuprofen), it may be desirable to dissolve those components in a non-aqueous carrier, and then admix that composition with the aqueous magnesium composition, including pharmaceutically acceptable dispersants and/or surfactants (as is typically done empirically), to provide the final product in the form of an emulsion; that is, essentially a cream or lotion including all of the active ingredients.

Other ingredients can include menthol and/or camphor as a mild anesthetic and counter-irritant in amounts up to about 1% and 4%, respectively, and zinc oxide as an astringent in amounts up to about 8%. The formulation may optionally include such ingredients as a penetration enhancer and CHC to prevent the formulation from running along the patient's skin (CHC thus acts essentially a viscosity modifier).

The magnesium compound, along with any of the optional ingredients, may be formulated as a liniment, lotion, suspension, emulsion, cream, ointment, gel, or foam, or as a liquid solution in a container or on a cotton absorbent applicator (such as the unit dose packages mentioned previously). A liniment is intended for external application and generally comprises an alcoholic solution of soap or an emulsion in admixture with oil; it is applied locally by rubbing on the affected area of the skin. Alcoholic liniments are used generally for their rubrifacient, counter-irritant, astringent, and penetrating effects (they typically include one or more aromatic compounds which may also enhance dermal penetration). A liniment is preferably applied in combination with massage to facilitate circulation in the massaged area and thus increase penetration of the magnesium and any other active ingredient(s) applied to the site. As described previously, these compositions may also include pharmaceutically and dermatologically acceptable colorants, fragrances, and/or texturizing agents.

The treatment of a condition such as arthritis with this novel composition preferably comprises applying the composition with magnesium salt at a 50% concentration to the affected area 1–5 times each day.

Treatment using the aforedescribed vibrational application includes applying a composition containing about 25% magnesium twice daily, and for each application massaging the affected area using a vibrator having a rate of about 5000 cycles per minute for a period of about 20–120 seconds (avoiding bony prominences).

In an other embodiment, the topical treatment just described can be supplemented with 300–900 mg./day of elemental magnesium (eg., an amount of a magnesium salt sufficient to deliver the noted amount of magnesium). In this treatment mode, supplemental calcium at a level of 300–600 mg/day is preferably given to prevent a relative calcium deficiency. Examples of magnesium compounds for oral administration include any one or combination of the magnesium salts described above. The preferred magnesium compound for oral administration is magnesium oxide.

Treatment of Periodontal Disease—Mouthwash and Toothpaste.

Periodontal disease is usually characterized by bacterial infection of gingival tissues, and is in part caused by dental plaque. *Streptococcus mutans* is the bacteria most commonly associated with gum inflammation and other aspects of gingivitis. The concomitant generation of plaque further irritates the gingival tissue, and the resulting degradation and inflammation creates a detrimental degenerative cycle.

It is believed that the novel topical compositions of the present invention for treating the oral cavity diminish or prevent plaque buildup, combat the bacterial infection, and also break the cycle of degranulation of white cells and further inflammation, analogous to the proposed theory described above (reliance upon which is not essential for practicing this invention).

According to this invention, a suitable oral composition for treating periodontal disease includes 10–50% preferably 50%, of magnesium sulfate; these amounts generally correspond to 0.8 to 6 mEq/ml, with the preferred amount being about 6 mEq/ml. Optional active ingredients include methyl salicylate and/or ibuprofen as described for the topical formulation for treating arthritis, in amounts of up to about 0.1%. It is hypothesized that the combination of magnesium compounds with conventional anti-inflammatory agents in the various compositions of this invention provide a synergistic therapeutic effect. Another optional ingredient is phenol, which functions as a local anesthetic, antiseptic, and bactericide, and further appears to assist in the penetration of the bacterial plaque. Further, sodium fluoride and/or stannous fluoride, in amounts up to 0.05% and 0.01% respectively, may be included as an anti-caries agent. Still further, oxygenating agents, such as perborates or peroxides (eg., hydrogen peroxide up to 5%, preferably 3%, or carbamide peroxide up to about 15%, preferably about 10%), can be added to effect cosmetic whitening of the teeth in addition to their antibacterial effects. Sanguinarine, an herbal extract, may also be included for its anti-plaque activity.

Typical inactive adjuvants include surfactants, such as polysorbate 80 (Tween 80), cetyl pyridinium chloride, Poloxamer 407, and sodium lauryl sulfate, may be added to assist in the access or penetration of the active ingredient(s) to the affected areas. Glycerin can be added as a humectant or demulcent and also to stabilize any peroxide compounds in the formulation. As before, conventional flavorants, colorants, fragrances, texturizers, stabilizers, preservatives, and the like, which are compatible with the composition and acceptable for oral use, can be included as desired.

The foregoing formulation may also be provided as a toothpaste (dentifrice) with the magnesium compound and any of the optional compounds as desired, in addition to the conventional dentifrice ingredients. Thus, the dentifrice may also contain polishes, mild abrasives, and the like. The dentifrice may be provided in a paste, gel, liquid, or powdered form.

Toothpaste

| Ingredient | | Wt. % |
|---|---|---|
| LAPONITE XLG (synthetic hectorite) | thickener | 3.00 |
| Xanthan Gum[6] | thickener/stabilizer | 0.15 |
| CMC[7] | thickener | 0.30 |
| Sorbitol 70%[8] | vehicle/sweetener | 55.00 |
| Magnesium Sulfate Heptahydrate USP | active ingredient | 15.00 |
| sodium lauryl sulfate (Empicol V3030) | surfactant/foaming agent | 1.00 |
| Ammonium Glycrrhizate 30%[9] | flavor modifier | 1.50 |
| Flavor | | 1.50 |
| Sodium Saccharine | sweetener | 0.20 |
| glycerine 96% | humectant | 10.00 |
| Titanium Dioxide | colorant | 1.00 |
| Hydrated Silica | abrasive | 10.00 |
| Water (D.I.) | vehicle | 1.35 |

[6]Keltrol SF grade, Kelco, Philadelphia, PA.
[7]Aqualon, Wilmington, DE.
[8]ICI Polyols, Wilmington, DE.
[9]McAndrews & Forbes, Camden, NJ.

If it is desired to add fluoride to the composition, it should be provided in a chelated form to avoid precipitating the fluoride due to the high magnesium content of the composition. Alternatively, the user can alternate between using the present dentifrice and a conventional one containing fluoride.

Mouthwash

| | | Wt. % |
|---|---|---|
| Magnesium Sulfate Heptahydrate USP | active ingredient | 25.00 |
| Water | vehicle | 58.59 |
| Sorbitol 70% | flavor adjunct/vehicle | 15.00 |
| Sodium Methyl Cocyl Taurate[10] | surfactant | 0.65 |
| Sodium Saccharine | flavor adjunct | 0.10 |
| Ammonium Glycrrhizate 30% | flavor adjunct | 0.25 |
| Carrubba A4110[11] | flavor | 0.35 |
| FDC Blue #1 0.05% | colorant | 0.06 |

[10]Finetex, Elmwood Park, NJ.
[11]Carrubba, Milford, CT.

A preferred regimen for treating periodontal disease is to brush at least twice daily for six months with the exemplified toothpaste, while using a mouthwash daily that contains at least 25% magnesium.

Using the aforementioned vibrational application, treatment of mild periodontal disease or caries should include (i) brushing with the toothpaste using an oscillating electric toothbrush (≈30,000 cycles per minute) for at least two minutes twice daily, (ii) rinsing with the mouthwash for 30 seconds twice daily (without eating or drinking for at least 20 minutes after each use), and (iii) massaging the gum at a vibration rate of about 5000 cycles per minutes for 30–60 seconds. For severe peridontal disease, in addition to the previously-described treatment steps, it is recommended that the patient soak the affected gum area for about 30–60 minutes with a sponge or cotton swab soaked with the mouthwash; soaking should be done once or twice daily.

Treatment of Asthma—Inhalational Therapy

The present compositions are also useful for treating asthma by administration via inhalation. Asthma is generally characterized as a hyper-reactivity of airway smooth muscle with an inflammatory response of the airway lining, and is often exacerbated by an accompanying secondary infection.

A solution containing 10–50% more preferably 20–30% of a magnesium compound, especially magnesium sulfate, is used as an active ingredient. The solution can also contain pharmaceuticals presently used for treating asthma, such as beta-adrenergic agents, which are useful in the treatment of periodic, chronic, and acute severe bronchospasm, and are also useful for prophylaxis against exercise-induced bronchospasm. Other optional active ingredients include corticosteroids and cromones; cromolyn sodium prevents degranulation of mast cells and the accompanying release of allergic reaction mediators, and corticosteroids are generally used as anti-inflammatories. Methylxanthine is a smooth muscle relaxant which also may be given as a systemic adjuvant as a bronchodilator. An inert odorant and/or flavorant may also be added if desired.

The solution containing the magnesium compound and any other ingredients is then provided, by known techniques, as a dispensing package that delivers a metered aerosol or nebulized solution of droplets of an appropriate particle size. In use, the composition is formulated to provide 10 mg. to 50 mg. of the magnesium compound per inhalational dose, generally effective to provide 20 mg. to 300 mg. per day of the magnesium compound. The formulation of optional active ingredients in the composition to provide effective, non-toxic doses thereof can be readily determined from the literature.

In a preferred embodiment, the inhalational therapy is combined with oral administration of magnesium, preferably as magnesium oxide, in an amount of 400–900 mg. of elemental magnesium, generally dispersed over 2–6 oral doses daily. Again, the administration of supplemental systemic calcium at a level of 300–600 mg/day is preferred to avoid relative calcium deficiency. Optional active ingredients for the oral supplement include beta-adrenergic compounds, corticosteroids, and occasionally methylxanthines (e.g., theophylline). The oral formulation can be provided as a capsule, tablet, elixir, or suspension.

Accordingly, the present inhalational therapy is seen to be a local treatment of asthma. This form of therapy is also useful for treating pharyngitis and rhinitis.

Dermatitis

The present compositions are useful for as anti-inflammatory agents in the treatment of chronic dermatitis and atopic dermatitis. A preferred composition includes 25% magnesium, especially dispersed in a topical ointment (e.g., CMC 9M31X5, available from Aqualon, Wilmington, Del., to which water has been added in a ratio of 1:1 by volume. One patient has used such a composition and found relief where only a partial response was found to the use of corticosteroids. Nevertheless, a combination of hydrocortisone and/or other corticosteroids along with antibiotic and antifungal agents in combination with the present compositions is also useful.

Relatively week solutions/dispersions of magnesium, such as 5–15%, in vehicles such as CMC or simethicone, are useful as a cold cream or other skin cream substitute.

Treating atopic dermatitis, chronic dermatitis, and neurodermatitis can be performed by applying a 25% magnesium composition to the affected area two to four times daily, and following each application with vibration for 20–120 seconds.

Treatment of Upper Respiratory Ailments

The formulations of this invention also find use in the temporary relief of the major symptoms of the common cold and certain respiratory allergies, such as nasal and sinus congestion, runny nose, sneezing, coughing, fever, and minor sore throat pain.

The composition may be formulated for inthalational delivery, such as via an inhaled nasal spray, as is common in present over-the-counter formulations. In general, the spray composition will comprise up to 50% by weight of magnesium sulfate, more preferably about 10% of the magnesium compound. Optional and preferred ingredients for a spray formulation include a decongestant as well as other conventional ingredients. Suitable decongestants include naphazoline HCl, an adrenergic and decongestant presently available under such trademarks as NAPHCON and PRIVINE HCl, and oxymetazoline HCl, a decongestant available under such trademarks as AFRIN and SINEX; oxymetazoline HCl is preferably present in amounts of up to about 0.1%, more preferably about 0.05% by weight of the composition. Additional ingredients for a nasal spray may comprise various preservatives (e.g., benzalkonium chloride, phenylmercuric acetate) and/or a soothing agent (such as glycine). Another optional addition for spray compositions is a corticosteroid, such as 0.5–2% hydrocortisone, and especially for treating severe or chronic rhinitis or sinusitis. The aqueous nasal spray is typically adjusted to be isotonic with the addition of NaCl.

In another embodiment, these formulations can be provided as an aqueous spray to the oropharynx cavity, especially for treating conditions such as pharyngitis (sore throat). These aqueous formulations comprise about 5–40%, preferably 10–30%, of the magnesium compound, and may be administered by using a spray pump. A preferred optional ingredient is phenol, at less than 2% by weight, as is presently available under the CHLORASEPTIC brand name; this product is also available in a spray pump dispenser as just noted for delivering the present formulations. Still further, these aqueous-based solutions may be provided in the form of a gargle.

These formulations for treating upper respiratory ailments may also be provided in the form of a tablet, soft gel capsule, or liquid (syrup). In these systemic formulations, preferable optional ingredients include&e an analgesic and/or antipyretic (e.g., acetaminophen at 325 mg per dose), a decongestant (such as pseudoephedrine HCl in effective amounts of about 30 mg per dose), an antihistamine (such as chlorpheniramine maleate or triprolidine HCl in effective amounts up to about 10 mg, more preferably about 5 mg per dose), and an antitussive (such as dextromethorphan HBr in effective amounts of up to about 20 mg, preferably about 10 mg per dose), and compatible and safe combinations thereof. When formulated primarily for allergy and sinus conditions, the antitussive is likely not required.

The novel magnesium formulations of this invention are also useful for yet a number of other conditions.

Treatment of Conjunctivitis—Ophthalmic Preparations.

For use as an eyewash in the treatment of inflammatory and allergic conditions, or for the treatment of conjunctivitis these novel compositions are preferably provided as a solution comprising 0.1% to 5% of magnesium sulfate. Cromolyn sodium in an amount of 0.1% to 5% can be included as an anti-allergic agent.

Such a formulation typically includes buffers, such as hydrochloric acid or potassium bicarbonate, to provide an optimal pH of about 7.4 (a pH range of 6 to 8 is generally acceptable). Conventional bacteriostatic preservatives such as benzalkonium chloride (up to about 0.02%) or benzathonium chloride (up to about 0.02%) can be included to maintain sterility. Antioxidants or stabilizers such as bisulfites or thiourea may be included in amounts up to about 0.5%, with an amount approximating 0.1% being preferred. Likewise, the osmotic pressure of the composition can be adjusted to isotonic with ingredients such as dextran 40 or dextran 70, glycerin, or sodium chloride can be added (dextrans are carbohydrate slimes, such as dextran 40, a polysaccharide having an average molecular weight of 40,000 and produced by the action of *Leuconostoc mesenteroides* on sucrose). Wetting or clarifying agents such as polysorbate 20 or 80 or Poloxamer 282, can also be added.

These ophthalmic preparations can be provided in liquid form for drop-wise administration, or can be formulated into a gel or ophthalmcally acceptable ointment base. Viscosity modifying agents such as carboxymethylcellulose, glycerin, polyethylene glycol, or a polysorbate can also be included to adjust the viscosity for easy self-administration by the patient.

Antihemorrhoidal Preparations.

Hemorrhoids, also called piles, are characterized by dilation and inflammation of veins (with or without thrombosis) in swollen or inflamed tissue at the margin of the anus or nearby within the rectum.

According to this invention, a preparation is prepared containing about 1–30%, more preferably 10–20%, of magnesium sulfate as the active anti-inflammatory and healing agent. Optional active ingredients include hydrocortisone (and derivatives thereof) in an effective amount up to about 3% (preferably at 1%) for reducing itching and inflammation. Ephedrine sulfate can be added as a vasoconstrictor to provide 2–25 mg. per dose. Calamine, white petrolatum, cocoa butter, cod liver oil, and the like can be included in amounts of up to about 50% to provide protectant, demulcent, and/or emollient effects. Calamine or zinc oxide, in amounts of 5–25%, can be present to provide an astringent effect.

These formulations are preferably provided as a cream, ointment, gel, or foam, and enema. Suppository or unit towelette dose formulations are also useful.

Treatment of Vaginal Infections—Vaginal Preparations.

The novel compositions of this invention are also useful to inhibit bacterial growth and reduce the occurrence and severity of vaginal infections and inflammation. The composition may be provided on a solid sorbent. Thus, in a preferred embodiment, a magnesium-containing solution is applied to a tampon or other catamenial device and allowed to dry. The final product should contain 1 mg to 100 mg of magnesium sulfate per tampon. Alternatively, the composition can be provided as a vaginal suppository also containing 1–100 mg of magnesium sulfate.

A relatively weak solution, e.g., 10% magnesium, can be used as a douche to provide an anti-inflammatory effect.

Skin Ulcers

Skin ulcers can be treated with a 5% magnesium, composition (e.g., dispersed in CMC) applied twice daily for two to three weeks.

Ulcerative Colitis Preparations.

Ulcerative colitis is an inflammatory disease of the colon with frequent exacerbations.

The topical treatment provided by this invention is achieved by administering an enema containing 0.1% to 5% by weight of magnesium sulfate to reduce the bacterial content and inflammation of the bowel, and to increase the blood flow to the affected area. The composition may also be provided in the form of a suppository for ulcerative proctitis.

Additional active ingredients for such a preparation can include anti-inflammatories such as prednisolone (10–50 mg per enema dosage) and antibiotics such as sulfasalazine.

Additional Local Administration.

The present formulations will likely be seen as useful for other conditions. For example, these formulations can be formulated for topical (dermal) application to treat eczema, psoriasis, neurodermatitis, contact dermatitis, seborrhea, and related skin conditions.

Analogous to the asthma treatment described above, these formulations of magnesium compounds are useful for treating such other pulmonary conditions as emphysema, chronic obstructive pulmonary disease, and chronic bronchitis; administration is likewise by inhalation using the asthma regimen as a guide.

Sedative Preparations.

The present invention also contemplates the administration of oral magnesium in combination with antihistamines or other sedating compounds as a sedative or sleep-inducing medication. In the preferred embodiment, magnesium oxide is taken orally in daily amounts of about 100 mg to 900 mg in combination with a conventional antihistamine such as chlorpheniramine maleate to promote drowsiness and thereby facilitate sleeps. As mentioned previously, it is preferred to jointly administer sufficient amounts of calcium systemically to avoid relative calcium deficiency when magnesium is given systemically (orally).

As described, in one aspect the present invention is directed to novel therapeutic formulations of magnesium compounds for topical administration. In another aspect, the invention is directed to a pharmacotherapeutic regimen that uses magnesium to enhance the effects of conventional drugs for treating a given condition. This beneficial enhancement of the conventional drug's action allows for less of the drug to be used, thereby reducing possible side effects as well as reducing the patient's costs for treatment (the magnesium compounds useful in the present treatments typically cost significantly less than the pharmaceuticals with which they are combined). A current philosophy in pharmacotherapeutic treatment is the administration of smaller amounts of a number of different agents to obtain the benefits of each while decreasing side-effects more common at higher doses. The present invention provides similar benefits by the addition of magnesium to a conventional pharmacotherapeutic regime, not only to provide therapeutic effects, but also to enhance the effects of the other active ingredients, thereby allowing for lower doses of those other ingredients.

The foregoing description and specific examples are meant to illustrate and describe the invention, and various alterations and modifications may become apparent to the skilled artisan upon reading this specification, and such changes are intended to be within the scope and spirit of the invention as defined by the appended claims.

What is claimed is:

1. A method for treating periodontal disease, which comprises the steps of administering to the oral cavity of a patient in need of such treatment a composition in the form of a dentifrice comprising a pharmaceutically acceptable aqueous-based vehicle and an effective amount of magnesium sulfate heptahydrate, wherein said vehicle is a pharmaceutically acceptable oral carrier, and wherein said magnesium compound is present in said composition an amount effective to provide a hypertonic concentration of the magnesium compound therein, said amount being from about 15% to about 50% by weight of the dentifrice composition.

2. The method defined by claim 1, wherein the amount of the magnesium compound is 15–30% by weight of the composition.

3. The method defined by claim 1, further comprising the step of applying said composition to the gums of a patient using vibrational application having a frequency of about 50–100 Hz.

4. The method defined by claim 1, wherein said composition is a toothpaste further comprising a cosmetically acceptable mild dental abrasive.

5. The method defined by claim 1, where said composition is a toothpaste or mouthwash further comprising a cosmetically acceptable foaming agent.

6. The method defined by claim 1, comprising providing said composition as a toothpaste and as mouthwash, first brushing with said toothpaste, and then washing with said mouthwash.

7. The method defined by claim 6, further comprising the oral administration of calcium.

8. The method defined by claim 6, further comprising massaging said patient's gums after washing using a vibrator having a rate of about 80–85 Hz.

9. A method of treating periodontal disease, which comprises the step of administering to the oral cavity of a patient a composition in the form of a mouthwash comprising a pharmaceutically acceptable aqueous-based vehicle and an effective amount of at least one magnesium compound highly soluble in said vehicle, wherein said vehicle is a pharmaceutically acceptable oral carrier, and wherein said magnesium compound is present in said composition an amount effective to provide a hypertonic concentration of the magnesium compound therein, said amount being from about 25% to about 50% by weight of the mouthwash composition.

10. A method of treating periodontal disease, which comprises the steps of:
   (i) administering to the oral cavity of a patient a composition in the form of a mouthwash, said composition comprising a pharmaceutically acceptable aqueous-based vehicle and an effective amount of magnesium sulfate heptahydrate, wherein said vehicle is a pharmaceutically acceptable oral carrier, and wherein said magnesium compound is present in said composition an amount effective to provide a hypertonic concentration of the magnesium compound therein, said amount being from about 25% to about 50% by weight of the mouthwash composition; and
   (ii) applying said composition to the patient's gums using vibrational application having a frequency of about 50–100 Hz.

11. A method of treating periodontal disease, which comprises the step of administering to the oral cavity of a patient a composition in the form of a mouthwash comprising a pharmaceutically acceptable aqueous-based vehicle and an effective amount of magnesium sulfate heptahydrate, wherein said vehicle is a pharmaceutically acceptable oral carrier, and wherein said magnesium compound is present in said composition an amount effective to provide a hypertonic concentration of the magnesium compound therein, said amount being from about 25% to about 50% by weight of the mouthwash composition, and wherein said composition further comprises a cosmetically acceptable foaming agent.

12. The method set forth in claim 10, further comprising the step of massaging said patient's gums using an article which vibrates at about 80–85 Hz.

* * * * *